United States Patent
Weng

(10) Patent No.: US 11,500,216 B2
(45) Date of Patent: Nov. 15, 2022

(54) METHOD AND DEVICE FOR ADJUSTING PUPIL DISTANCE OF VIRTUAL REALITY DISPLAY DEVICE

(71) Applicant: PIMAX TECHNOLOGY (SHANGHAI) CO., LTD, Shanghai (CN)

(72) Inventor: Zhibin Weng, Shanghai (CN)

(73) Assignee: PIMAX TECHNOLOGY (SHANGHAI) CO., LTD, Shanghai (CN)

( * ) Notice: Subject to any disclaimer, the term of this patent is extended or adjusted under 35 U.S.C. 154(b) by 46 days.

(21) Appl. No.: 16/965,027

(22) PCT Filed: Jan. 28, 2019

(86) PCT No.: PCT/CN2019/073504
§ 371 (c)(1),
(2) Date: Jul. 27, 2020

(87) PCT Pub. No.: WO2019/149175
PCT Pub. Date: Aug. 8, 2019

(65) Prior Publication Data
US 2021/0109356 A1  Apr. 15, 2021

(30) Foreign Application Priority Data

Jan. 30, 2018 (CN) .......................... 201810092477.5

(51) Int. Cl.
*G02B 27/01* (2006.01)
*G06F 3/01* (2006.01)

(52) U.S. Cl.
CPC ..... *G02B 27/0179* (2013.01); *G02B 27/0176* (2013.01); *G06F 3/013* (2013.01);
(Continued)

(58) Field of Classification Search
CPC ............ G02B 27/0171; G02B 27/0179; G02B 2027/0185; G02B 2027/0187; G02B 27/0176; G06F 3/013
See application file for complete search history.

(56) References Cited

U.S. PATENT DOCUMENTS

| | | | |
|---|---|---|---|
| 2013/0077049 A1* | 3/2013 | Bohn | G02B 27/017 351/210 |
| 2013/0258486 A1 | 10/2013 | Ionescu et al. | |
| 2014/0274391 A1* | 9/2014 | Stafford | H04N 13/383 463/32 |

FOREIGN PATENT DOCUMENTS

| | | |
|---|---|---|
| CN | 104216841 A | 12/2014 |
| CN | 104822061 A | 8/2015 |

(Continued)

OTHER PUBLICATIONS

First Office Action issued in counterpart Chinese Patent Application No. 201810092477.5, dated Aug. 2, 2019.
(Continued)

*Primary Examiner* — Alexander Eisen
*Assistant Examiner* — Cory A Almeida
(74) *Attorney, Agent, or Firm* — Westbridge IP LLC

(57) ABSTRACT

Disclosed are a method and device for adjusting a pupil distance of a virtual reality display device. The method adjusts a second pupil distance on a virtual reality display device by means of a first pupil distance of a user wearing the virtual reality display device, the first pupil distance referring to a pupil distance of the user wearing the virtual reality display device, and the second pupil distance being used as a distance between focal points of two lenses of the virtual reality display device; the method comprises: detecting whether the first pupil distance and the second pupil distance match; if the first pupil distance and the second pupil distance do not match, then executing a preset match-
(Continued)

ing operation on the virtual reality display device. The present application solves the technical problem of a virtual reality display device being bulky and heavy.

6 Claims, 6 Drawing Sheets

(52) U.S. Cl.
    CPC ............... *G02B 2027/0185* (2013.01); *G02B 2027/0187* (2013.01)

(56) References Cited

FOREIGN PATENT DOCUMENTS

| CN | 107506036 A | * 12/2017 | ......... G02B 27/0093 |
|----|-------------|-----------|------------------------|
| CN | 107506036 A | 12/2017   |                        |
| CN | 108170283 A | 6/2018    |                        |

OTHER PUBLICATIONS

International Search Report issued in corresponding PCT Application No. PCT/CN2019/073504, dated May 6, 2019.
Wirtten Opinion issued in corresponding PCT Application No. PCT/CN2019/073504, dated May 6, 2019.

* cited by examiner

METHOD AND DEVICE FOR ADJUSTING PUPIL DISTANCE OF VIRTUAL REALITY DISPLAY DEVICE

Application No. 201810092477.5, named "Method and Device for Pupillary Distance Regulation of Virtual Reality Display Device", was filed with the National Intellectual Property Administration on Jan. 30, 2018. All the disclosed contents of the priority of this Chinese invention patent are referenced herein.

TECHNICAL FIELD

This application relates to the technical field of virtual reality (VR) and, specifically, a method and device for pupillary distance regulation of VR display device.

BACKGROUND ART

VR display device is a type of 3D VR and observation equipment. It can be separately connected to the host to receive the 3D VR image signals from the host and utilize space tracker and positioner to observe the VR export effects.

As the inventor discovers, a VR display device normally requires manual regulation of pupillary distance. Such a method of regulation is rather subjective and normally leads to misalignment of the pupil center, lens center and screen (after screen splitting) center. As a result, the visual effects are poor and the problem of unclear and distorted image arises, thus reducing the user experience. Meanwhile, manual regulation requires considerable room, which causes the VR display device to be bulky and heavy.

No effective solution has been proposed to the problem of bulky and heavy VR display device.

Scope of Invention

The main purpose of this application is to disclose a method and device for pupillary distance regulation of virtual reality display device in order to address the problem of bulky and heavy VR display device.

In order to realize the foregoing purpose, one method for pupillary distance regulation of virtual reality display device is provided according to one part of this application.

The method for pupillary distance regulation of virtual reality display device under this application comprises: regulating the second pupillary distance of said VR display device as per the first pupillary distance of the user of said VR display device; said first pupillary distance refers to the pupillary distance of the user of said VR display device; said second pupillary distance works as the distance between the foci of two lenses on said VR display device; said method comprises testing if said first pupillary distance and said second pupillary distance match each other; if said first pupillary distance and said second pupillary distance don't match each other, preset matching operations will be conducted on said VR display device.

Further, said preset matching operations comprise: measuring the first pupillary distance; comparing if the first pupillary distance and the second pupillary distance match each other; if said first pupillary distance and said second pupillary distance don't match each other, regulate said first pupillary distance and said second pupillary distance in the following steps until they match each other: regulate the central point of the screen of said VR display device so that said central point of screen is aligned with the focus of the lens of said VR display device; cause said central point, the focus of lens of said VR display device and the two pupils of said user to be aligned.

Further, said measurement of the first pupillary distance comprises: acquiring an image of user eyes; processing said eye images; determining the position information of the central points of the left pupil and the right pupil; measuring the distance between the central points of said left pupil and said right pupil.

Further, regulation of said central point of screen until said central point is aligned with the focus of lens of said VR display device comprises: regulating the lens on said VR display device; said lens is connected to the slide rheostat; turning the displacement of said lens into electric signals via said slide rheostat; transmitting said electric signals to the microcontroller of said VR display device. Further, alignment of said central point, the focus of lens of said VR display device and the two pupils of said user comprises: said microcontroller turning the electric signals of said slide rheostat into distance signals; said microcontroller instructing said screen to move in the following manner as per said distance signals: said screen moves to said central point and becomes aligned with the focus of lens of said VR display device and the two pupils of said user.

In order to realize the foregoing purposes, one pupillary regulation device of VR display device is provided according to another part of this application.

The pupillary regulation device of VR display device under this application comprises: a test unit, configured to measure if said first pupillary distance matches with said second pupillary distance; said first pupillary distance is the user's pupillary distance; said second pupillary distance is the distance between the two lenses' foci of said VR display device; a matching unit, configured to conduct the preset matching operations of said VR display device if said first pupillary distance don't match with said second pupillary distance.

Further, said matching unit comprises: a measuring module, configured to measure the first pupillary distance; a matching module, configured to measure if said first pupillary distance matches with said second pupillary distance; a first regulating module, configured to regulate said second pupillary distance until it matches with said first pupillary distance if said second pupillary distance doesn't match with said first pupillary distance and then transmit it to said microcontroller; a second regulating module, configured to regulate the central point of the screen of said VR display device until said central point is aligned with the lens focus of said VR display device and said central point, the lens focus of said VR display device and the two pupils of said user are aligned.

Further, said first regulating module is configured to regulate said second pupillary distance until said second pupillary distance matches with said first pupillary distance; transmit the electric signals to said microcontroller.

Further, said second regulating module is configured to regulate said central point until said central point is aligned with the lens focus of said VR display device; and said central point, the lens focus of said VR display device and the two pupils of said user are aligned.

In order to realize the foregoing purposes, one VR display device is provided according to the third part of this application.

In order to realize the foregoing purposes, one pupillary distance regulation method of VR display device is provided according to the fourth part of this application.

The method for pupillary distance regulation of virtual reality display device under this application comprises: regulating the second pupillary distance of said VR display device as per the first pupillary distance of the user of said VR display device; said first pupillary distance refers to the pupillary distance of the user of said VR display device; said second pupillary distance works as the distance between the focuses of two lenses on said VR display device; said method comprises testing if said first pupillary distance and said second pupillary distance match each other; if said first pupillary distance and said second pupillary distance don't match each other, preset matching operations will be conducted on said VR display device. Said preset matching operations comprise: regulating the two lenses on said VR display device until the distance between the focuses of two lenses is the same as said first pupillary distance; regulating the central points of the two screens of said VR display device as per the displacement of the two lenses until the two central points are aligned with the focuses of said two lenses.

Further, measuring if said first pupillary distance and said second pupillary distance match each other comprises: measuring the first pupillary distance; comparing if the first pupillary distance and the second pupillary distance match each other.

Further, said measurement of the first pupillary distance comprises: acquiring an image of user eyes; processing said eye images; determining the position information of the central points of the left pupil and the right pupil; measuring the distance between the central points of said left pupil and said right pupil.

Further, said regulation of the central points of two screens of said VR display device as per the displacements of said two lenses until the central points of said two screens are aligned with the foci of said two lenses comprises: regulating the movement of lenses on said VR display device and connecting said lenses to the slide rheostat; said slide rheostat turning the displacement of said lenses into electric signals and transmitting said electric signals to the microcontroller of said VR display device; said microcontroller calculating the displacement of said lenses according to said electric signals and generating control signals according to the calculated displacement of said lenses to control the movement of said central points until said central points are aligned with the focuses of said lenses.

In order to realize the foregoing purposes, one pupillary distance regulation device of VR display device is provided according to the fifth part of this application.

The pupillary regulation device of VR display device under this application comprises:

A test unit, configured to measure if said first pupillary distance matches with said second pupillary distance; said first pupillary distance is the user's pupillary distance; said second pupillary distance is the distance between the two lens focuses of said VR display device;

A matching unit, configured to conduct the preset matching operations of said VR display device if said first pupillary distance don't match with said second pupillary distance.

Further, said test unit comprises: a measuring module, configured to measure the first pupillary distance; a comparing module, configured to compare if said first pupillary distance matches with said second pupillary distance;

Further, said matching unit comprises: a first regulating module, configured to regulate the movements of two lenses on said VR display device until the distance between the focuses of said two lenses is the same as said first pupillary distance; a second regulating module, configured to regulate the movements of the central points of two screens of said VR display device according to the displacement of said two lenses until the central points of said two screens are aligned with the focuses of said two lenses.

The VR display device under this application comprises: the pupillary distance regulation device specified in any of the foregoing items.

In embodiments of this application, the goal of regulating the pupillary distance of the VR display device is realized via a pupillary distance regulation device through the combination of testing, matching and regulation, thus achieving the technical effect of reducing the volume and weight of the VR display device and addressing the technical problem of bulky and heavy VR display device.

DESCRIPTIONS OF ATTACHED DRAWINGS

As part of the application, the attached drawings work to deepen understanding of this application so that other characteristics, purposes and strengths of this application become more evident. The schematic diagrams of the application's embodiments and their descriptions are used to explain this application but shall not constitute improper restrictions on this application. In the attached drawings.

SPECIFIC EMBODIMENTS

To make those in the art better understand the solution disclosed by this application, a clear and complete description of the technical solution of embodiments of this application will be provided below with reference to the attached drawings. Apparently, said embodiments are just part of the embodiments of this application. Based on the embodiments specified herein, all other embodiments acquired by those with ordinary skills in the art without creative labors shall also be within the scope of protection of this application.

It is noteworthy that "first" and "second" as specified in the specifications, the claims and the foregoing attached drawings are used to differentiate similar objects but shall not denote any specific sequence or order. It shall be understood that the data used in this manner are interchangeable under certain circumstances for the convenience of the embodiments introduced herein. Moreover, "include" and "has" and any of their modifications shall not be exclusive of others. For instance, the process and method that includes a series of steps or units shall not be limited to the steps or units clearly specified herein but may also include other steps or units that are not clearly listed herein or are inherent to those processes, methods, products or equipment. In this application, the orientation or position relations indicated by the term "upper" are the orientation or position relations based on the attached drawings. These terms are primarily used to better describe the application and its embodiments but shall not restrict the target device within a specific orientation or within the formation and operation in a specific orientation.

Moreover, part of the foregoing terms may also be used to denote meanings other than orientation or position relations. For instance, term "upper" may also indicate affiliations or connections under certain circumstances. Those with ordinary skills in the art can understand the meaning of these terms in this application as the case may be.

Moreover, "configure", "connect" and "link" shall be understood in a broad sense. For instance, "connect" may be fixed connection, removable connection or integrated formation; it may be direct connection or connection via a medium or the interconnection between two devices, elements or constituents. Those with ordinary skills in the art can understand the meaning of these terms in this application as the case may be.

It is noteworthy that the embodiments and the characteristics therein may be combined with one another in the absence of conflict. The application will be introduced below with reference to the attached drawings and the embodiments.

Figure 1:
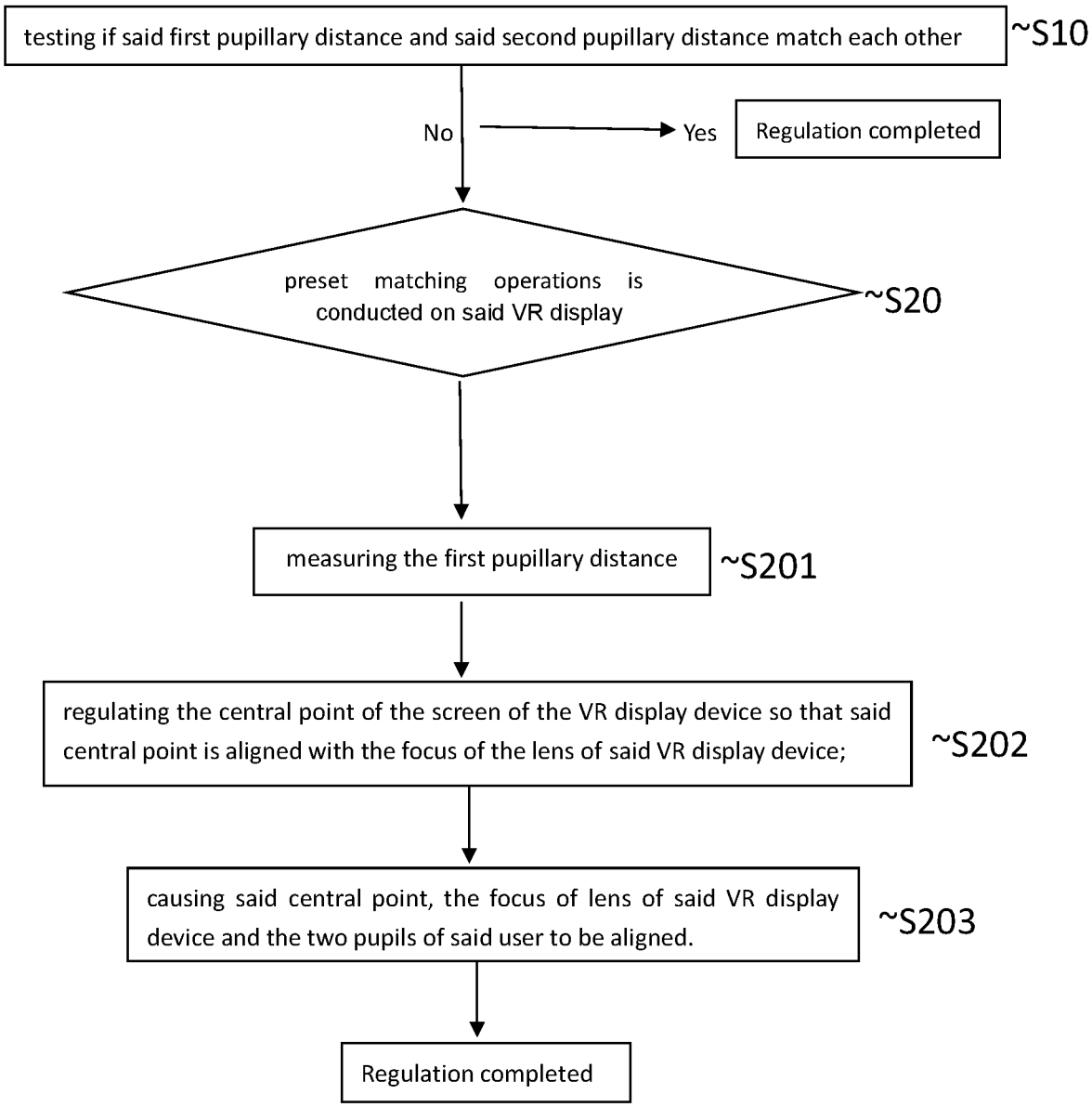
FIG. 1 is the process flow chart of the pupillary regulation method of one embodiment under this application.

As FIG. 1 shows, this application relates to the technical field of virtual reality (VR) display device. Said pupillary regulation method regulates the second pupillary distance of said VR display device as per the first pupillary distance of the user of said VR display device; said first pupillary distance refers to the pupillary distance of the user of said VR display device; said second pupillary distance works as the distance between the foci of two lenses on said VR display device; said method comprises:

Step S10, testing if said first pupillary distance and said second pupillary distance match each other; if said first pupillary distance and said second pupillary distance don't match each other, Step S20 preset matching operations will be conducted on said VR display device.

It is noteworthy that said Step S20 preset matching operations comprises: Step S201 measuring the first pupillary distance; Step S202 comparing if the first pupillary distance and the second pupillary distance match each other; if said second pupillary distance and said first pupillary distance don't match each other, continue to implement Step S203 regulating the central point of the screen of the VR display device so that said central point is aligned with the focus of the lens of said VR display device; finally, implement Step S204 causing said central point, the focus of lens of said VR display device and the two pupils of said user to be aligned.

Figure 2:
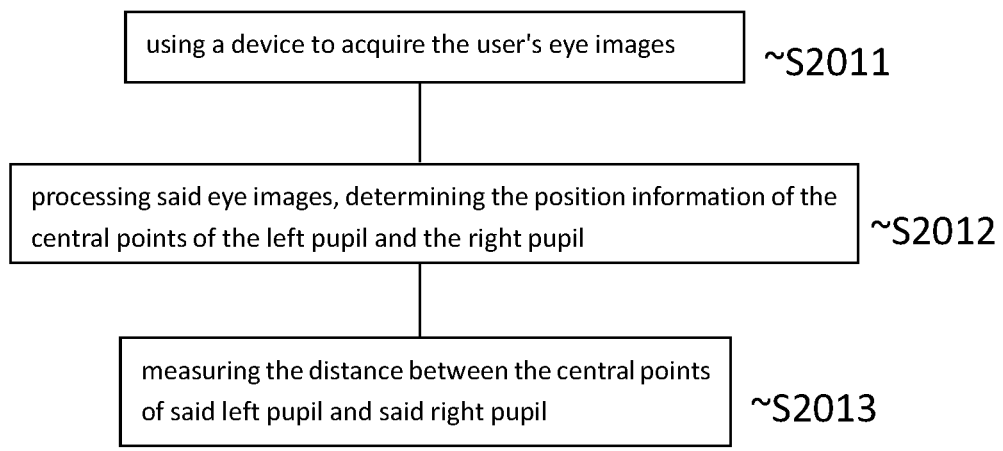
FIG. 2 is the process flow chart of the measurement of the first pupillary distance of one embodiment under this application.

As FIG. 2 shows, S201 measuring the first pupillary distance specifically comprises the following steps:

Step S2011, using a device to acquire the user's eye images, e.g. using a pupillary distance meter or another device to acquire images of the user's eyes;

Step S2012, processing said eye images, determining the position information of the central points of the left pupil and the right pupil; the pupillary distance meter can determine the positions of both pupils on the image;

Step S2013, the pupillary distance meter can measure the distance between the central points of said left pupil and said right pupil which is the pupillary distance of the user, i.e. the first pupillary distance.

As another embodiment of this application, testing if said first pupillary distance and said second pupillary distance match each other comprises: measuring the first pupillary distance; comparing if the first pupillary distance and the second pupillary distance match each other.

Wherein, said measuring the first pupillary distance comprises: acquiring images of user eyes; processing said eye images; determining the position information of the central points of the left pupil and the right pupil; measuring the distance between the central points of said left pupil and said right pupil.

Preset matching operations of said VR display device comprise:

Regulating the movements of two lenses on said VR display device until the distance between the focuses of said two lenses is the same as said first pupillary distance;

Regulating the movements of the central points of two screens of said VR display device according to the displacement of said two lenses until the central points of said two screens are aligned with the focuses of said two lenses respectively.

Wherein, said regulating the movements of the central points of two screens of said VR display device according to the displacement of said two lenses until the central points of said two screens are aligned with the focuses of said two lenses respectively comprises:

Regulating the movements of lens on said VR display device; said lens is connected to the slide rheostat;

Said slide rheostat turning the displacement of said lens into electric signals and transmitting said electric signals to the microcontroller of said VR display device;

Said microcontroller calculating the displacement of said lenses according to said electric signals and generating control signals according to the calculated displacement of said lenses to control the movement of said central points until said central points are aligned with said lenses.

Figure 3:
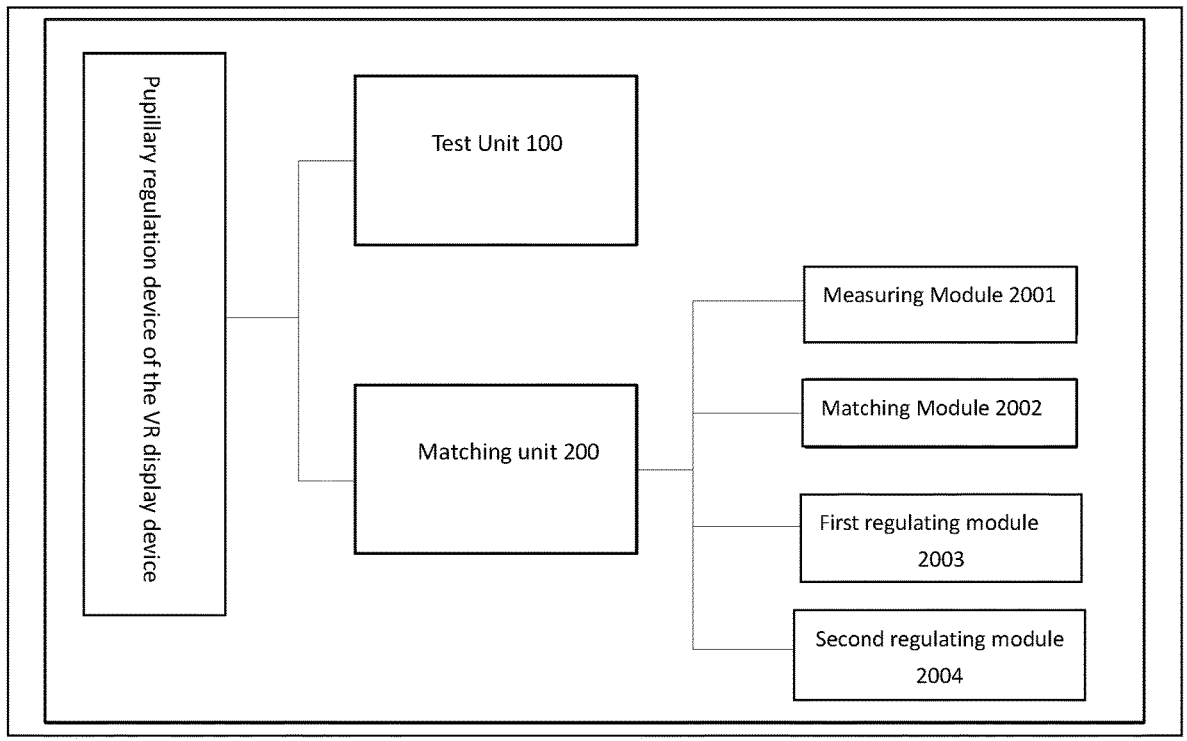
FIG. 3 is the structural diagram of the pupillary distance regulation device of one embodiment under this application.

As FIG. 3 shows, the pupillary regulation device of VR display device under this application comprises: test unit 100 and matching unit 2002, wherein test unit 100 is configured to measure if said first pupillary distance matches with said second pupillary distance; the pupillary distance regulation is completed if they match; matching unit 200 will be launched if they don't match.

Matching unit 200 specifically comprises:

Measuring module 2001, configured to measure the first pupillary distance, including using the method of S201;

Matching module 2002, configured to measure if the first pupillary distance matches with the second pupillary distance, i.e. comparing the acquired first pupillary distance of the user with the second pupillary distance of the VR display device. They match each other if they conform to each other. They don't match each other otherwise;

First regulating module 2003, configured to regulate and match said first pupillary distance and said secondary pupillary distance if they don't match each other; move the lens of the VR display device until the lens' central point is aligned with the user's pupils; transmit the displacement signals of the lens to said microcontroller;

Second regulating module 2004, configured to regulate the central point of the screen of said VR display device until said central point is aligned with the lens focus of said VR display device; and finally said central point, the lens focus of said VR display device and the two pupils of said user are aligned.

It is noteworthy that first regulating module 2003 is configured to regulate said second pupillary distance until said second pupillary distance matches with said first pupillary distance. The matching process comprises moving the lens of the VR display device; turning the lens's displacements into electric signals via the slide rheostat; and transmitting said electric signals to said microcontroller.

Moreover, second regulating module 2004 is configured to regulate said central point of screen until said central point of screen is aligned with the lens focus of said VR display device; the microcontroller transmits the electric signals to the screen movement control part of the VR display device to regulate the screen movement. Finally, the central point of screen, the lens focus of VR display device and the two pupils of user are aligned.

As another embodiment of this application, the pupillary distance regulation device of this VR display device comprises: a test unit, configured to measure if said first pupillary distance matches with said second pupillary distance; said first pupillary distance is the user's pupillary distance; said second pupillary distance is the distance between the two lenses' foci of said VR display device; and a matching unit, configured to conduct the preset matching operations of said VR display device if said first pupillary distance don't match with said second pupillary distance.

Wherein, the test unit comprises:

A measuring module, configured to measure the first pupillary distance;

A comparing module, configured to compare if the first pupillary distance matches with the second pupillary distance.

Wherein, the matching unit comprises:

A first regulating module, configured to regulate the movements of two lenses of said VR display device until the distance between the foci of said two lenses is the same as said first pupillary distance;

A second regulating module, configured to regulate the movements of the central points of two screens of said VR display device according to the displacement of said two lenses until the central points of said two screens are aligned with the focuses of said two lenses.

Figure 4:
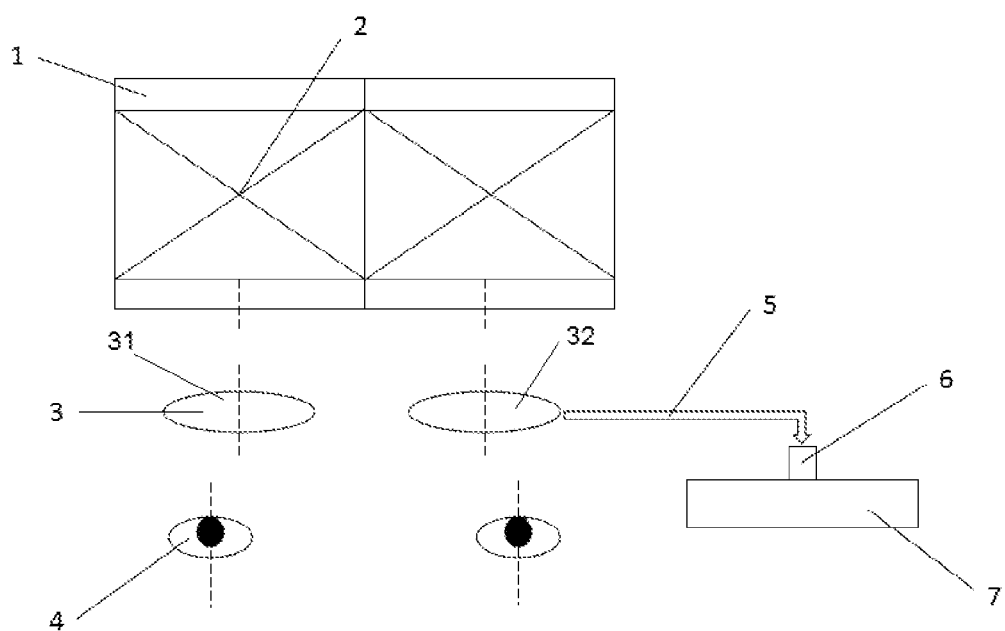
FIG. 4 is the schematic diagram of the pre-regulation state for the pupillary distance regulation method of one embodiment under this application.

As FIG. 4 shows, the pupillary distance regulation device disclosed by this application comprises: VR display device screen 1, VR display device screen central point 2, lens 3, connecting part 5, slide rheostat slider 6 and slide rheostat 7. For the convenience of introducing the embodiment, 4 is user's eye.

As preferred in this embodiment, lens 3 comprises first lens 31 and second lens 32 which are connected to slide rheostat 7. When first lens 31 and second lens 32 move, slider 6 of slide rheostat will move to generate two displacement signals and thus two electric signals.

Connecting part 5 and lens 3 are interconnected, including but not limited to bolted, buckle and other flexible connections as well as welded and other fixed connections. The movement of lens 3 is transmitted to slide rheostat 7 via connecting part 5.

As preferred in this embodiment, the screen of the VR display device has one left central point and one right central point which are aligned with first lens 31 and second lens 32 respectively for regulation of pupillary distance of screen.

As preferred in this embodiment, connecting part 5 and slider 6 of slide rheostat are interconnected, including but not limited to bolted, buckle and other flexible connections as well as welded and other fixed connections to realize control of slider 6 of slide rheostat.

Move lens 3 which drives slider 6 of slide rheostat to move and generate a certain displacement on slide rheostat 7. Slide rheostat 7 turns this displacement signal into an electric signal and thus realizes signal conversion.

Figure 5:
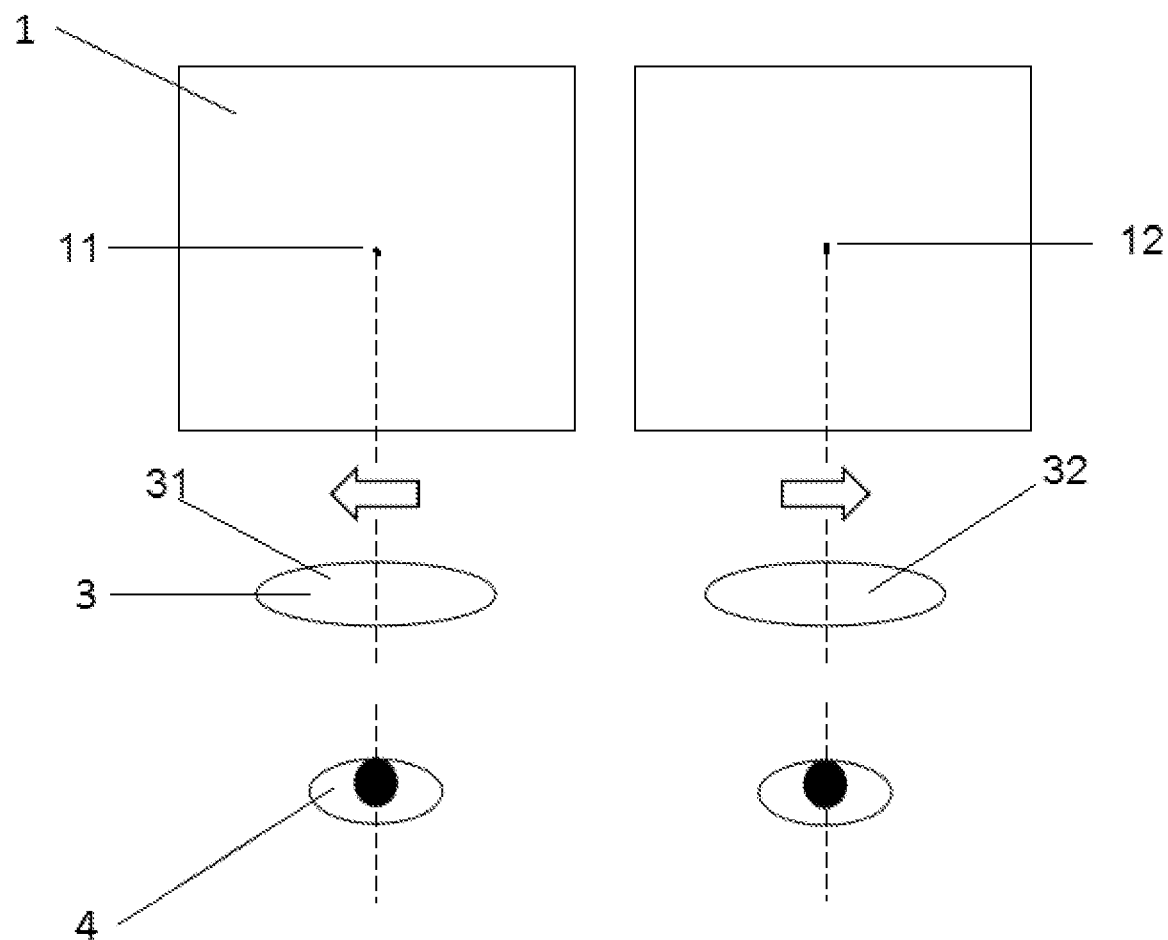
FIG. 5 is the schematic diagram of the post-regulation state for the pupillary distance regulation method of one embodiment under this application.

As FIG. 5 shows, regulate first lens 31 and second lens 32 until the pupillary distance of lens 3 is aligned with user's eyes 4. Finally, the two lenses are aligned with the user's two pupils respectively.

Figure 6:
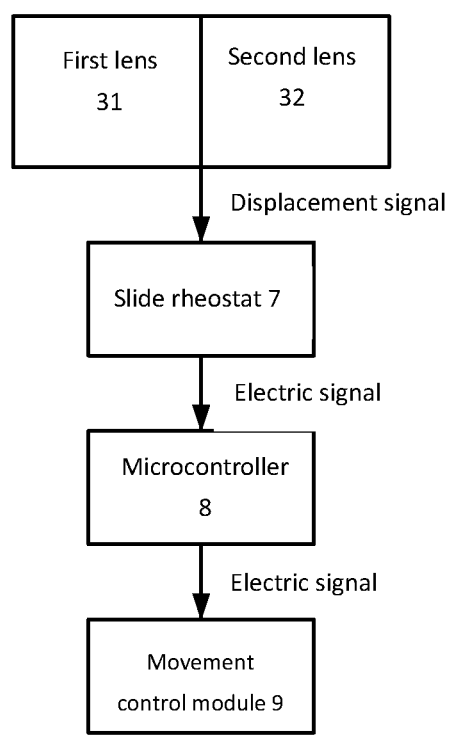
FIG. 6 is the schematic diagram of the signal transmission process of the pupillary distance regulation device of one embodiment under this application.

As FIG. 6 shows, slide rheostat 7 and microprocessor are interconnected. Slide rheostat 7 turns said displacement signals into electric signals.

The first screen central point 11 on the VR display device screen receives the first lens displacement signals from the microcontroller, e.g. with a displacement of 0.1 mm of the first lens, the first central point of screen will also move by 0.1 mm.

The second screen central point 12 on the VR display device screen receives the second lens displacement signals from the microcontroller, e.g. with a displacement of 0.1 mm of the second lens, the second central point of screen will also move by 0.1 mm.

The screen of the VR display device further comprises movement control module 9, configured to control the movement of screen central point on the VR display device; electric signals are transmitted by microcontroller 8 to screen movement control module 9 of the VR display device; screen movement control module 9 sends a movement order to control the movement of the central point of the screen and thus realize alignment of the screen central point with the central point of lens 3.

As illustrated above, this application achieves the following technical effects: the pupillary distance of VR display device is conveniently regulated via one set of pupillary distance regulation method and device. This method doesn't require subjective regulation. Meanwhile, addition of microcontroller and slide rheostat substantially reduces the volume and weight of the VR display device.

The foregoing are just preferred embodiments of this application and shall not restrict this application. Those with ordinary skills in the art can make various modifications to and changes of this application. However, all such modifications, equivalent substitutions and improvements shall be within the scope of protection of this application if they conform to the spirits and principles of this application.

INDUSTRIAL UTILITY

The pupillary distance regulation method of this application can be used in a VR display device. This pupillary regulation method regulates the second pupillary distance of the VR display device as per the first pupillary distance of the user of the VR display device; the first pupillary distance refers to the pupillary distance of the user of the VR display device; the second pupillary distance works as the distance between the focuses of two lenses on said VR display device. If the first pupillary distance and the second pupillary distance don't match each other, preset matching operations will be conducted on the VR display device. A microcontroller and a slide rheostat are added into the pupillary distance regulation device for automatic regulation of the central points on the screen of the VR display device. It has a high regulating accuracy. Meanwhile, the screen of the VR display device is fixed to reduce the volume and weight of the VR display device, improve the user experiences and enhance the market competitiveness of the VR display device furnished with this method.

The invention claimed is:

1. A method for pupillary distance regulation of a virtual reality display device that is characterized in that a second pupillary distance of the VR display device is regulated as per a first pupillary distance of a user of the VR display device; the first pupillary distance refers to a pupillary distance of the user of the VR display device; the second pupillary distance works as the distance between the focuses of two lenses on the VR display device; the method comprises:
  testing if the first pupillary distance and the second pupillary distance match each other;
  if the first pupillary distance and the second pupillary distance don't match each other, preset matching operations will be conducted on the VR display device;
the preset matching operations comprises:
measuring the first pupillary distance;
comparing if the first pupillary distance and the second pupillary distance match each other;
  if the second pupillary distance and the first pupillary distance don't match each other, regulating the second pupillary distance according to the following steps so that the second pupillary distance matches with the first pupillary distance:
  regulating the central point of the screen of the VR display device so that the central point is aligned with the focus of the lens of the VR display device;
  causing the central point of the screen, the focus of lens of the VR display device and the two pupils of the user to be aligned;
  wherein causing the central points of screen, the lenses' foci of the VR display device and the two pupils of the user to be aligned comprises: a microcontroller turning the electric signals of a slide rheostat into distance signals; the microcontroller instructing the screen to move in the following manner as per the distance signals: the screen moves to the central points of the screen and becomes aligned with the focus of lens of the VR display device and the two pupils of the user.

2. The method for pupillary distance regulation of virtual reality display device of claim 1, wherein the measuring the first pupillary distance comprises:
  acquiring an image of user eyes;
  processing the eye images; determining the position information of the central points of the left pupil and the right pupil;
  measuring the distance between the central points of a left pupil and a right pupil.

3. The method for pupillary distance regulation of virtual reality display device of claim 1, wherein the regulation of the central points of screens of the VR display device until the central points of the screens are aligned with the focuses of the two lenses comprises:
  regulating the movement of lenses on the VR display device and connecting the lenses to the slide rheostat;
  the slide rheostat turning the displacement of the lenses into electric signals;
  transmitting the electric signals to the microcontroller of the VR display device.

4. A pupillary regulation method of a VR display device that is characterized in that it regulates a second pupillary distance of the VR display device as per a first pupillary distance of the VR display device; the first pupillary distance refers to the pupillary distance of a user of the VR display device; the second pupillary distance works as the distance between the foci of two lenses on the VR display device; the method comprises:
  testing if the first pupillary distance and the second pupillary distance match each other;
  if the first pupillary distance and the second pupillary distance don't match each other, preset matching operations will be conducted on the VR display device; the preset matching operations comprise:
  regulating the movements of two lenses on the VR display device until the distance between the foci of two lenses is the same as the first pupillary distance;
  regulating the movements of central points of the two screens of the VR display device, as per the displacement of the two lenses until the two central points are aligned with the foci of the two lenses and the two pupils of the user;
  the regulating the movements of the central points of two screens of the VR display device as per the displacements of the two lenses until the central points of the two screens are aligned with the foci of the two lenses comprises:
  regulating the movement of lenses on the VR display device and connecting the lenses to a slide rheostat; the slide rheostat turning the displacement of the lenses into electric signals and transmitting the electric signals to a microcontroller of the VR display device; the microcontroller calculating the displacement of the lenses according to the electric signals and generating control signals according to the calculated displacement of the lenses to control the movement of the central points until the central points are aligned with the foci of the lenses the two pupils of the user and the two pupils of the user.

5. The pupillary regulation method of claim 4, wherein the measuring if the first pupillary distance and the second pupillary distance match each other comprises:
  measuring the first pupillary distance;
  comparing if the first pupillary distance and the second pupillary distance match each other.

6. The pupillary regulation method of claim 5, wherein the measuring the first pupillary distance comprises:
  acquiring an image of user eyes;
  processing the eye images; determining the position information of the central points of a left pupil and a right pupil;
  measuring the distance between the central points of the left pupil and the right pupil.

* * * * *